(12) United States Patent
Neumann

(10) Patent No.: US 12,009,085 B2
(45) Date of Patent: Jun. 11, 2024

(54) SYSTEMS AND METHODS FOR SCHEDULING ALIMENTARY COMBINATIONS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 23 days.

(21) Appl. No.: 16/939,268

(22) Filed: Jul. 27, 2020

(65) Prior Publication Data
US 2022/0028526 A1   Jan. 27, 2022

(51) Int. Cl.
*G16H 20/60* (2018.01)
*G06F 16/2457* (2019.01)
(Continued)

(52) U.S. Cl.
CPC ....... *G16H 20/60* (2018.01); *G06F 16/24578* (2019.01); *G06Q 10/1093* (2013.01);
(Continued)

(58) Field of Classification Search
CPC ........ G16H 20/60; G16H 50/20; G16H 10/60; G09B 19/0092; A63B 2220/20; A63B 2230/75; G06F 16/24578; G06Q 10/1093
(Continued)

(56) References Cited

U.S. PATENT DOCUMENTS 7,894,849 B2   2/2011   Kass et al.
8,409,104 B2   4/2013   Cobain
(Continued)

FOREIGN PATENT DOCUMENTS

WO   2018020239   2/2018

OTHER PUBLICATIONS

Westerman, et al.; Longitudinal analysis of biomarker data from a personalized nutrition platform in healthy subjects; Scientific Reports; Oct. 2, 2018; https://www.nature.com/articles/s41598-018-33008-7.pdf.
(Continued)

*Primary Examiner* — Mamon Obeid
*Assistant Examiner* — Teresa S Williams
(74) *Attorney, Agent, or Firm* — Caldwell Intellectual Property Law

(57) ABSTRACT

A system for scheduling alimentary combinations includes a computing device configured to provide an alimentary instruction set including a plurality of target nutrient quantities corresponding to a plurality of scheduled meals, determine a per-meal alimentary instruction set as a function of the plurality of target nutrient quantities, receive, from each alimentary provider device of a plurality of alimentary provider devices, a plurality of provider ingredient combinations, generate a ranked list of ingredient combinations as a function of the plurality of provider ingredient combinations, receive a user selection of a provider ingredient combination corresponding to a meal of the plurality of scheduled meals, and generate a modified ranked list of ingredient combinations as a function of the user selection and the alimentary instruction set.

20 Claims, 6 Drawing Sheets

(51) Int. Cl.
*G06Q 10/1093* (2023.01)
*G09B 19/00* (2006.01)
*G16H 10/60* (2018.01)
*G16H 50/20* (2018.01)

(52) U.S. Cl.
CPC ......... *G09B 19/0092* (2013.01); *G16H 10/60* (2018.01); *G16H 50/20* (2018.01)

(58) Field of Classification Search
USPC ........................................................ 434/127
See application file for complete search history.

(56) References Cited

U.S. PATENT DOCUMENTS

| | | | |
|---|---|---|---|
| 8,532,938 | B2 | 9/2013 | Jung et al. |
| 8,737,971 | B2 | 5/2014 | Van Rooyen |
| 8,762,167 | B2 | 6/2014 | Blander et al. |
| 8,822,225 | B2 | 9/2014 | Gotch et al. |
| 9,132,219 | B2 | 9/2015 | Akonur et al. |
| 9,183,757 | B2 | 11/2015 | Yamada et al. |
| 9,589,480 | B2 | 3/2017 | Ellis et al. |
| 9,758,839 | B2 | 9/2017 | Apte et al. |
| 9,838,508 | B2 | 12/2017 | Salem |
| 10,102,345 | B2 | 10/2018 | Yanev et al. |
| 10,127,361 | B2 | 11/2018 | Hyde et al. |
| 10,133,849 | B2 | 11/2018 | Yanev et al. |
| 2008/0177149 | A1 | 7/2008 | Weinert et al. |
| 2008/0195594 | A1 | 8/2008 | Gerjets et al. |
| 2008/0306763 | A1 | 12/2008 | James |
| 2010/0098809 | A1 | 4/2010 | Bender et al. |
| 2013/0079612 | A1 | 3/2013 | Hunt et al. |
| 2013/0138447 | A1 | 5/2013 | Nova et al. |
| 2014/0214590 | A1* | 7/2014 | Argue ................ G06Q 30/0631 705/26.7 |
| 2015/0012295 | A1 | 1/2015 | Mahoney |
| 2016/0042152 | A1 | 2/2016 | Oran |
| 2017/0216518 | A1 | 8/2017 | Davis et al. |
| 2018/0032698 | A1 | 2/2018 | Lau et al. |
| 2018/0233064 | A1* | 8/2018 | Dunn ................ G06F 16/9535 |

OTHER PUBLICATIONS

Inside Tracker; Who we are; file:///C:/Users/LindseyPowell/Downloads/InsideTracker's%20expert%20team_%20scientists...pdf.

Bald, Eric; The A.I. Diet; https://www.weizmann-usa.org/news-media/in-the-news/the-ai-diet.

Ramachandran, Swaroopini; Mar. 15, 2019; The algorithm to a perfect diet-AI has answers; http://peasonmoss.com/2019/03/15/the-algorithm-to-a-perfect-diet-ai-has-answers/.

Vk, Anirudh; 5 AI-Powered fitness startups in India who are using data science to promote healthy lifestyle; https://www.analyticsindiamag.com/5-ai-powered-fitness-startups-in-india-who-are-using-data-science-to-promote-healthy-lifestyle/.

\* cited by examiner

SYSTEMS AND METHODS FOR SCHEDULING ALIMENTARY COMBINATIONS

FIELD OF THE INVENTION

The present invention generally relates to the field of network communication and processing. In particular, the present invention is directed to systems and methods for scheduling alimentary combinations.

BACKGROUND

Existing solutions for selection of a best fit for alimentary provisioning based upon physiological dictates have generally avoided dealing with the multiplicity of possible solutions by limiting sources or possible selections. This can lead to frustration and under-utilization, which can negate many of the benefits of such solutions.

SUMMARY OF THE DISCLOSURE

In an aspect, a system for scheduling alimentary combinations includes a computing device configured to provide an alimentary instruction set including a plurality of target nutrient quantities corresponding to a plurality of scheduled meals, determine a per-meal alimentary instruction set as a function of the plurality of target nutrient quantities, receive, from each alimentary provider device of a plurality of alimentary provider devices, a plurality of provider ingredient combinations, generate a ranked list of ingredient combinations as a function of the plurality of provider ingredient combinations, wherein generating includes determining a nutrient listing corresponding to each ingredient combination of the plurality of provider ingredient combinations, creating a distance metric from the nutrient listing to the per-meal alimentary instruction set, and selecting at least an ingredient listing that minimizes the distance metric, and ranking the plurality provider ingredient combinations to minimize the distance metric, receive a user selection of a provider ingredient combination corresponding to a meal of the plurality of scheduled meals, and generate a modified ranked list of ingredient combinations as a function of the user selection and the alimentary instruction set.

In another aspect, a method of scheduling alimentary combinations includes providing, by a computing device, an alimentary instruction set including a plurality of target nutrient quantities corresponding to a plurality of scheduled meals. The method includes determining, by the computing device, a per-meal alimentary instruction set as a function of the plurality of target nutrient quantities. The method includes receiving, by the computing device, from each alimentary provider device of a plurality of alimentary provider devices, a plurality of provider ingredient combinations. The method includes generating, by the computing device, a ranked list of ingredient combinations as a function of the plurality of provider ingredient combinations, wherein generating includes determining a nutrient listing corresponding to each ingredient combination of the plurality of provider ingredient combinations, creating a distance metric from the nutrient listing to the per-meal alimentary instruction set, and selecting at least an ingredient listing that minimizes the distance metric, and ranking the plurality provider ingredient combinations to minimize the distance metric. The method includes receiving, by the computing device, a user selection of a provider ingredient combination corresponding to a meal of the plurality of scheduled meals. The method includes generating, by the computing device, a modified ranked list of ingredient combinations as a function of the user selection and the alimentary instruction set.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments disclosed herein schedule ingredient combinations according to a degree to which they match nutritional recommendations, as well as user selections. Ingredient combinations may be ranked according to degree of match to nutritional recommendations, which may include ranking by category such as meal type; ingredient combinations may be recommended over a scheduled period, which recommendations a user may accept or override. In embodiments, ranking, recommendation, and/or user selection may be iterative, filling in a series of meals in a schedule to fit nutritional recommendations and user selections.

Figure 1:
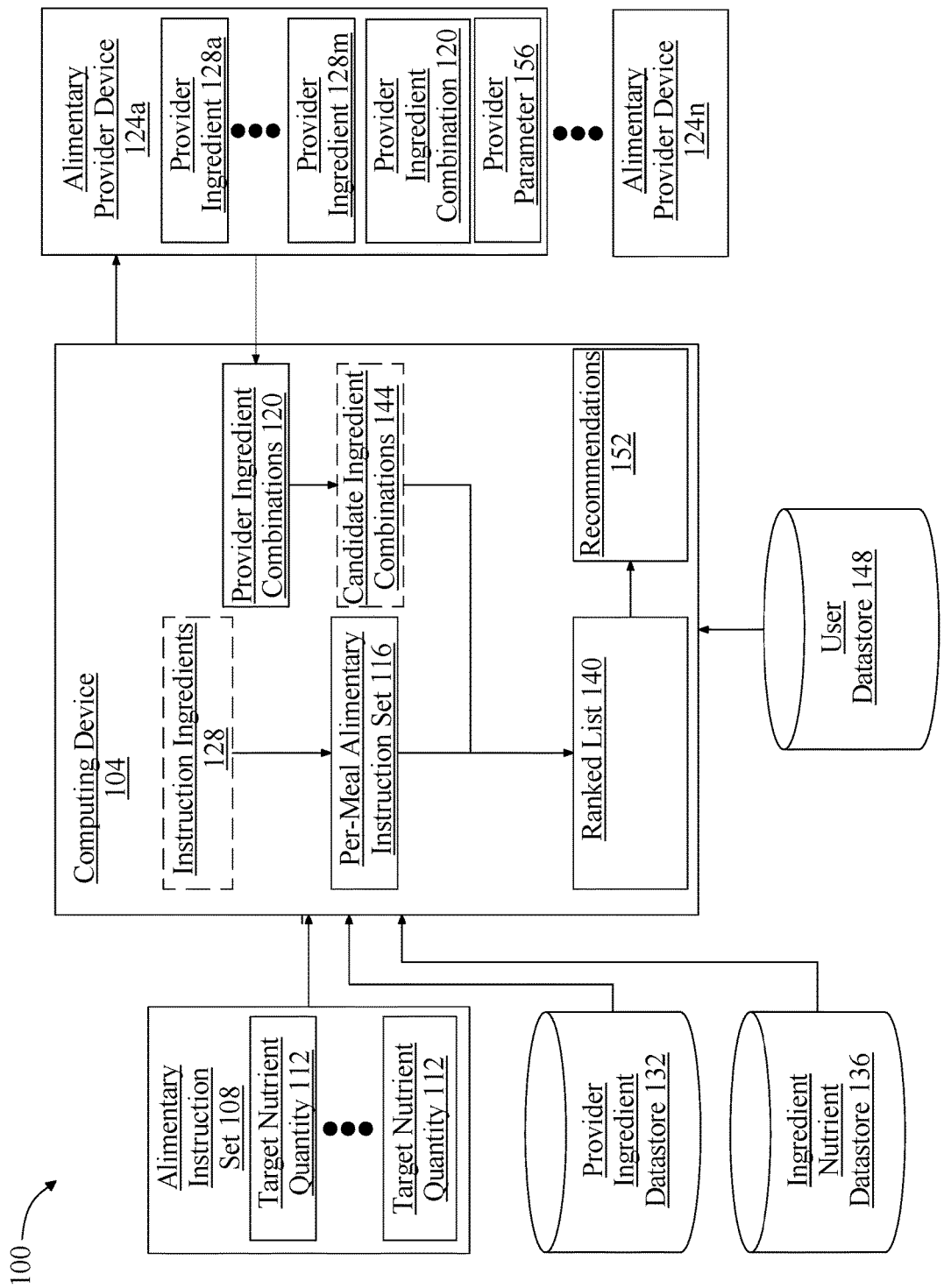
FIG. 1 is a block diagram of an exemplary embodiment of a system for alimentary provisioning.

Referring now to FIG. 1, an exemplary embodiment of a system 100 for alimentary provisioning is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to provide an alimentary instruction set 108 including a plurality of target nutrient quantities 112 corresponding to a plurality of scheduled meals. As used in this disclosure, an "alimentary instruction set" is a list or other collection of nutritional recommendations 152 for a user, including recommendations 152 of foods, nutrients, ingredients, and/or quantities thereof, that a user should consume for improved and/or optimal health. As used in this disclosure, a "target nutrition quantity" is a quantity of a given nutrient that alimentary instruction set 108 recommends user to consume. Quantities may include numbers representing a maximal amount to be consumed, a minimal amount to be consumed, and/or a precise amount that is determined to be ideal. Quantity may be zero for a nutrient that a user should not receive, and/or for a nutrient having no positive health benefit; for instance, a user who is diabetic may be recommended a quantity of zero for glucose, sucrose, or the like.

Further referring to FIG. 1, "scheduled meals" as used in this disclosure are meals scheduled to be consumed at one or more dates and times. Dates and times may be defined and/or recorded as data in any suitable way; for instance and without limitation, dates and times may be specific, such as 5:00 on Wednesday, Oct. 22, 2029, approximate, such as approximately 5:00 on Wednesday, Oct. 22, 2029, defined as falling within a range, such as between 3 and 7 on Wednesday, Oct. 22, 2029, and/or defined as a type of meal, such as supper on Wednesday, Oct. 22, 2029. A plurality of scheduled meals may pertain to a plurality of meals to be consumed over a certain period of time such as a day, week, or month; for instance, plurality of meals may define all meals and snacks to be consumed contiguously within such a period.

Figure 2:
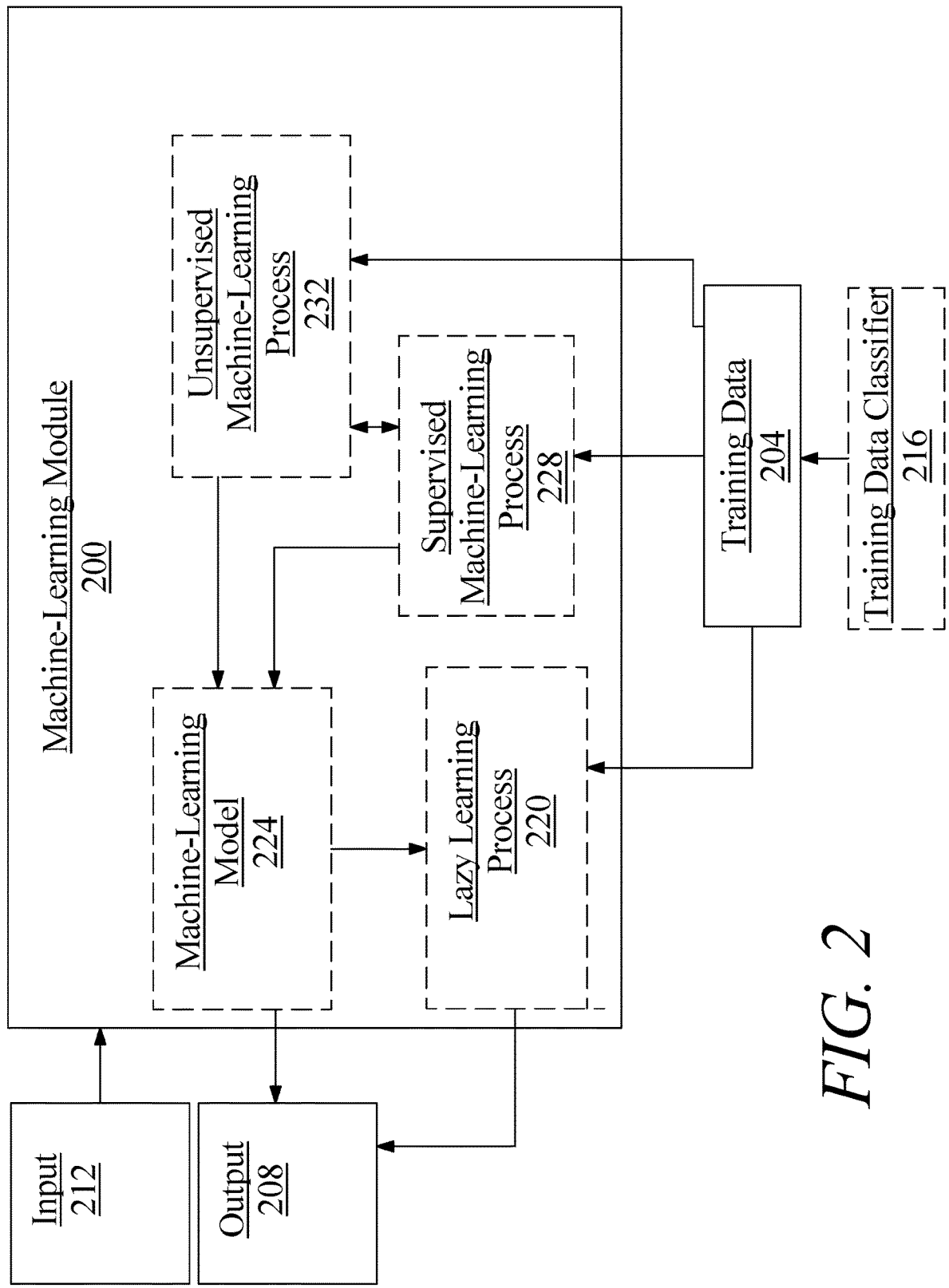
FIG. 2 is a block diagram of an exemplary embodiment of a machine-learning module.

With continued reference to FIG. 1, computing device 104 may provide alimentary instruction set 108 using a machine-learning process. Referring now to FIG. 2, an exemplary embodiment of a machine-learning module 200 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device 104/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device 104 and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to user cohorts, classes and/or categories of ingredient combinations, or the like.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning model 224s. A "machine-learning model 224," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Referring again to FIG. 1, computing device 104 may provide alimentary instruction set 108 by receiving training data, recording at least a biological extraction from a user, training a machine-learning process using the training data, and, generating the at least an alimentary instruction set 108 as a function of biological extraction and using the machine-learning process. Generation of alimentary instruction set 108 using machine learning may be implemented, without limitation, as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Alternatively or additionally, alimentary instruction set 108 may be received from user, from a medical professional, a nutritionist, and/or from one or more remote devices, including devices operated by user, by a medical professional, or the like. At least a biological extraction may include any element and/or elements of data suitable for use as at least an element of physiological state data. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor may be configured to detect internal and/or external biomarkers and/or readings. At least a sensor may be a part of system or may be a separate device in communication with system.

Still referring to FIG. 1, computing device 104 may determine a per-meal alimentary instruction set 116 as a function of the plurality of target nutrient quantities 112. As used in this disclosure, a "per-meal alimentary instruction set" is a plurality of target nutrient quantities 112 as described above for a single meal of a plurality of scheduled meals. Per-meal alimentary instruction set 116 may be generated using any suitable process, including without limitation by dividing each target nutrient quantity 112 of plurality of nutrient quantities by a number of scheduled meals.

With continued reference to FIG. 1, computing device 104 may receive a plurality of provider ingredient combinations 120 from each alimentary provider device of a plurality of alimentary provider devices 124a-n. A "provider ingredient combination," is defined for the purposes of this disclosure as a combination of ingredients, which may be referred to as provider ingredients 128a-m that an alimentary provider and/or alimentary provider device indicates may be provided, for instance and without limitation in the form of a meal kit. An alimentary provider device may include any device suitable for use as computing device 104, as described above, which is operated by an alimentary provider. A provider ingredient combination 120 may include, without limitation a "meal kit," defined as an ingredient combination to be prepared by an end user; preparation may include heating and/or reheating a cooked meal, combining ingredients, chopping ingredients, marinating ingredients, and/or any other process of transforming ingredients into a meal. A meal kit may come with instructions for preparation. A meal kit may instruct that users add water or other elements that may be external to meal kit and/or provided by user.

Further referring to FIG. 1, an "alimentary provider," as used in this disclosure, is a person or entity that prepares alimentary products such as meals, food items, and/or drinks, including without limitation a restaurant, a food delivery service, or the like. Provider ingredients of provider ingredient combinations 120 may include any ingredient or ingredients, where "ingredients" are defined as any ingredient in any alimentary product. In an embodiment, each alimentary provider device may indicate a time period, such as a date range, during which each ingredient is available, a geographic region within which each ingredient is available, or the like; alternatively or additionally, each alimentary provider device may solely indicated current availability of each ingredient and/or report only ingredients that are available from an alimentary provider associated with the alimentary provider device at the time that transmission occurs. Computing device 104 may store received provider ingredients in a provider ingredient datastore 132. Provider ingredient datastore 132 may include any data structure for ordered storage and retrieval of data, which may be implemented as a hardware or software module. A provider ingredient datastore 132 may be implemented, without limitation, as a relational database, a key-value retrieval datastore such as a NOSQL database, or any other format or structure for use as a datastore that a person skilled in the art would recognize as suitable upon review of the entirety of this disclosure. A provider ingredient datastore 132 may include a plurality of data entries and/or records as described above. Data entries in a provider ingredient datastore 132 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a provider ingredient datastore 132 may reflect categories, cohorts, and/or populations of data consistently with this disclosure. Provider ingredient datastore 132 may be located in memory of computing device 104 and/or on another device in and/or in communication with system 100.

Figure 3:
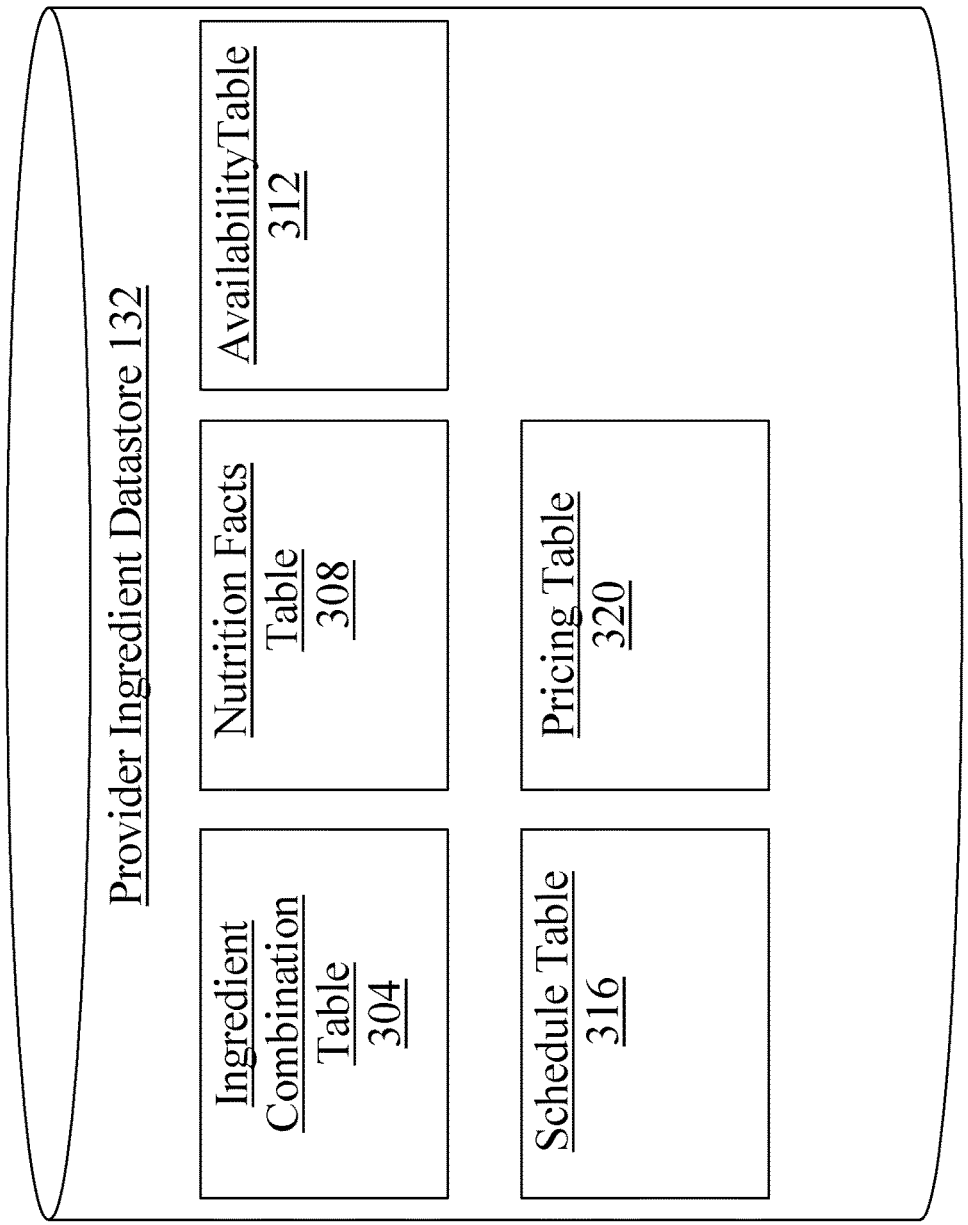
FIG. 3 is a block diagram of an exemplary embodiment of a provider ingredient datastore 132.

Referring now to FIG. 3, provider ingredient data store may include an ingredient combination table 304, which may list ingredients used in each ingredient combination. Provider ingredient data store may include nutrition facts table 308, which may list nutrition quantities present in one or more ingredients and/or ingredient combinations; this may be used for comparison and distance metric and described in further detail herein. Provider ingredient data store may include an availability 312, which may indicate ingredients and/or ingredient combinations that are currently available. Provider ingredient data store may include a schedule table 316, which may indicate when ingredients and/or ingredient combinations are and/or have been available, for instance on a seasonal basis and/or according to production by one or more suppliers. Provider ingredient data store may include a pricing table 320, which may describe prices for ingredients and/or ingredient combinations.

Referring again to FIG. 1, computing device 104 may group provider ingredients within provider ingredient data store according to a geographical region in which the provider ingredients are available, a time period during which the provider ingredients are available, and/or any other category that may be defined by data associated with any provider ingredient as described in this disclosure. Provider ingredients may be grouped in provider ingredient datastore 132 according to identifiers of alimentary provider devices 124*a-n*, and/or associated alimentary providers, that transmitted provider ingredients; in other words, computing device 104 and/or other devices in and/or communicating with system 100 may be able to query provider ingredient datastore 132 using an identifier of an alimentary provider and receive in return a list of ingredients currently available to that provider and/or that will be available to that alimentary provider within a given time period and/or at a particular location.

Further referring to FIG. 1, computing device is configured to generate a ranked list 140 of ingredient combinations as a function of the plurality of provider ingredient combinations 120. A "ranked list," as used in this disclosure, is an ordered collection of data elements for which an order of presentation is defined according to ascending or descending values of a quantitative or other textual field associated with each element in the ordered collection. Computing device 104 may accomplish this, without limitation, by determining a nutrient listing corresponding to each ingredient combination of the plurality of provider ingredient combinations 120, for instance as retrieved from provider ingredient datastore 132.

Still referring to FIG. 1, computing device 104 may create a distance metric from nutrient listing to per-meal alimentary instruction set 116. Distance metric may be computed between provider ingredients and/or nutrient quantities associated therewith, and one or more nutrient quantities associated with provider ingredient combinations 120, and/or provider ingredient combinations 120. Computing device 104 may identify one or more instruction ingredients, which may include any ingredients suitable for use as provider ingredients as described above, using an ingredient nutrient datastore 136, which may be implemented using any datastore suitable for use as provider ingredient datastore 132. Ingredient nutrient datastore 136 may associate each ingredient of a plurality of ingredients with one or more nutrients contained in the ingredient, as well as amounts of each such nutrient available per a given quantity of the ingredient, such that querying ingredient nutrient datastore 136 using one or more nutrients provided in alimentary instruction set 108 may return a list of ingredients containing the one or more nutrients; query may be implemented as a compound query, that returns ingredients containing selected combinations of nutrients as well as a single query returning any ingredients containing a single nutrient, or the like. Such ingredients may be transmitted to each alimentary provider device, permitting alimentary provider device and/or a user thereof to indicate each ingredient, of the instruction set ingredients, that alimentary provider is able to use and/or procure. In an embodiment, this may enable alimentary providers to indicate not only ingredients that they currently have in stock, but also ingredients they are able to acquire in a timely manner. Computing device 104 may receive from each alimentary provider device, a plurality of matching ingredients. In an embodiment, alimentary provider devices 124*a-n* may provide both a list of ingredients currently offered, as described above, and a set of selections of instruction ingredients as described above. Computing device 104 may identify plurality of instruction ingredients as a function of the target nutrient quantities 112 using ingredient nutrient datastore 136.

Continuing to refer to FIG. 1, computing device 104 may select each ingredient combination of plurality of ingredient combinations by determining a nutrient listing corresponding to each ingredient combination of the plurality of ingredient combinations, creating a distance metric from the nutrient listing to the alimentary instruction set 108, and selecting at least an ingredient listing that minimizes the distance metric, and ranking alimentary combinations according to a degree to which each minimizes the distance metric. A "distance metric," as used in this disclosure, is a quantitative value indicating a degree of similarity of a set of data values to another set of data values. For instance, and without limitation, combinations of nutrient quantities associated with each ingredient combination, and target nutrient quantities 112 of alimentary instruction set 108, may be represented a vector. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance metric may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting illustration, target nutrients from alimentary instruction set 108, and/or one or more subsets thereof, may be represented using a vector or other data structure, and nutrients provided by each ingredient combination of plurality of ingredient combinations may be represented by a like data structure, such as another vector; a distance metric comparing the two data structures may then be calculated and compared to distance metrics calculations to find a minimal distance metric calculation and/or a set of minimal distance metric calculations. A set of minimal distance metric calculations may be a set of distance metric calculations less than a preconfigured threshold distance from data structure representing target nutrients. Preconfigured threshold may be set by one or more expert users and/or determined statistically, for instance by finding a top quartile and/or number of percentiles of proximity in a series of distance metric determinations over time for user, at one time for a plurality of users, and/or over time for a plurality of users. Plurality of users may include a plurality of users selected by a user classifier, which may classify user to a plurality of users having similar physiological data and/or user data; implementation of a user classifier may be performed, without limitation, as described in U.S. Nonprovisional application Ser. No. 16/865,740, filed on May 4, 2020 and entitled "METHODS AND SYSTEMS FOR SYSTEM FOR NUTRITIONAL RECOMMENDATION USING ARTIFICIAL INTELLIGENCE ANALYSIS OF IMMUNE IMPACTS," the entirety of which is incorporated herein by reference. In an embodiment, a distance metric may include a measurement of an optimization of one or more factors that include distance, price, quality and/or availability.

In an embodiment, and further referring to FIG. 1, neutral ingredients and/or neutral nutrients may be excluded from data structures used in distance metric calculations and/or classification as described in further detail below. A "neutral ingredient" as used in this disclosure is an ingredient that has not been determined to have a measurable negative or positive effect on health, such as some seasonings, spices, or the like. In an embodiment, system 100 may not map neutral ingredients to nutrients; for instance, ingredient nutrient datastore 136 may not list nutrients for a neutral ingredient. Alternatively or additionally a nutrient having no measurable positive or negative health effect, referred to for purposes of this disclosure as a "neutral nutrient," may be listed in ingredient nutrient datastore 136, but excluded from distance metric and/or classification calculations. As a non-limiting example, two foods having ingredients differing only by neutral ingredients and/or neutral nutrients may thus be treated by system 100 as equivalent.

Still referring to FIG. 1, distance metric may be determined using a distance metric of a classifier. A "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)+P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements. KNN algorithm may operate according to any suitable distance metric, including without limitation vector similarity as described above.

Continuing to refer to FIG. 1, classifier may be trained by computing device 104 and/or other devices in system using training data associating nutrient quantities and/or sets of nutrient quantities to ingredient combinations recorded as having been used, for instance, in meals and/or servings in the past. Classifier may generate a plurality of categories of combinations of nutrients, each including at least one target nutrient quantity 112 matching alimentary instruction set 108, and may classify ingredient combinations to such categories; in an embodiment, ingredient combinations classified to categories closer to alimentary instruction set 108 according to distance metric may be labeled as beneficial ingredient combinations.

With further reference to FIG. 1, computing device 104 is configured to rank plurality provider ingredient combinations 120 to minimize the distance metric, where "ranking to minimize" indicates conferring a higher ranking to a device that corresponds to a smaller distance metric. In embodiments, ranking may be performed according to meal category; for instance, ranking may be performed within breakfast meals, lunch meals, dinner meals, or the like.

Still referring to FIG. 1, computing device 104 may be configured to filter plurality of provider ingredients according to one or more goal parameters. For instance, computing device 104 may identify a plurality of candidate ingredient combinations 144 as a function of the plurality ingredients, where candidate ingredient combinations 144 are any provider ingredient combinations 120 not eliminated by a filtering process. Computing device 104 may then generate ranked list 140 as a function of plurality of candidate ingredient combinations 144, according to any process described above for generation of ranked list 140. Identifying plurality of candidate ingredient combinations 144 may include elimination of one or more provider ingredient combinations 120 that diverge too greatly from alimentary instruction set 108. For instance, and without limitation, computing device 104 may compare a distance metric corresponding to each provider ingredient combination to a preconfigured threshold, which may be any quantitative value representing a minimum, maximum, and/or range of acceptable distance metric values, and eliminate each ingredient combination that fails the threshold comparison, where "failing" indicates without limitation being less than a minimal threshold, more than a maximal threshold, and/or outside a range defined by a threshold. As a further non-limiting example, identifying plurality of candidate ingredient combinations 144 may include receiving at least a user parameter and identifying the plurality of candidate ingredient combinations 144 to match the at least a user parameter.

Still referring to FIG. 1, computing device 104 may alternatively or additionally filter candidate ingredient combinations 144 according to one or more goal parameters and/or user entries. For instance, user may specify a desired meal, and computing device 104 may eliminate candidate ingredient combinations 144 that do not match the user entry; as further non-limiting examples, candidate ingredient combinations 144 that do not match user entries specifying a user maximal price, a maximal wait and/or transport time, or the like may be eliminated as well. Such filtration may be followed by presentation of filtered candidate ingredient combinations 144 to user, and/or further selection of at least a recommended ingredient combination using additional processes such as loss function use as described above.

In an embodiment, and still referring to FIG. 1, one or more candidate ingredient combinations 144 and/or recommended ingredient combinations may be filtered out and/or eliminated prior to presentation to user if the one or more candidate ingredient combinations 144 and/or recommended ingredient combinations are determined to violate a user-specific proscription. A "user-specific proscription," as used in this disclosure, is an element of data indicating that a user cannot receive an ingredient, nutrient, and/or combination of ingredients. A user-specific proscription may include, without limitation, a health-related reason the user receive and/or consume the ingredient, nutrient, and/or combination of ingredients, such as an allergy, sensitivity, or other medical condition such as without limitation phenylketonuria, a medical condition preventing participation in an activity and/or receipt of a pharmaceutical product, a moral, religious, and/or philosophical prohibition on receipt of thereof, or the like. User-specific proscriptions may include as a non-limiting example, restrictions imposed by kosher and/or halal dietary rules.

With continued reference to FIG. 1, one or more user-specific proscriptions and/or one or more additional user data may stored in and/or retrieved from a user datastore 148. User datastore 148 may be implemented in any manner suitable for implementation of provider ingredient datastore as described above.

Figure 4:
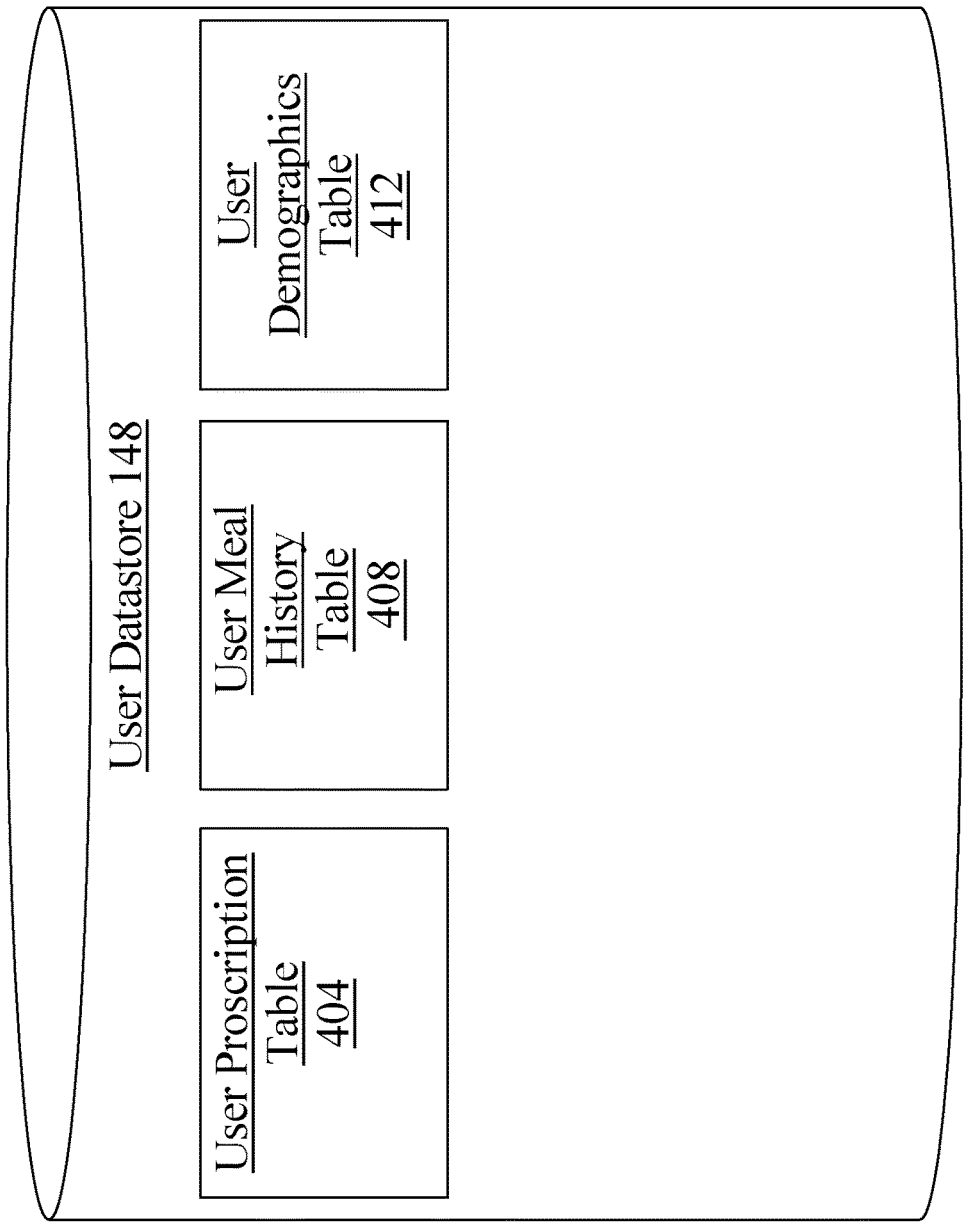
FIG. 4 is a block diagram of an exemplary embodiment of a user datastore 148.

Referring now to FIG. 4, an exemplary embodiment of a user datastore 148 is illustrated. User datastore may include, without limitation, a user proscription table 404, where user proscriptions as described in further detail below may be stored. User datastore 148 may include a user meal history table 408, where a history and/or listing of past user meals may be stored. User datastore 148 may include a user demographics table 412, in which one or more elements of demographic information pertaining to user, as without limitation ethnicity, national origin, age, language, sex, geographic location of residence, or the like may be stored. Persons skilled in the art, upon reviewing the entirety of this disclosure, will be aware of various data that may be stored in user datastore and/or tables in which data may be stored.

Continuing to refer to FIG. 1, computing device 104 may be configured to receive a user selection of a provider ingredient combination corresponding to a meal of the plurality of scheduled meals and receiving a user selection an element of the displayed ranked list 140. In an embodiment, computing device 104 may display the ranked list 140 on a user client device. Displaying may include displaying according to rank order, for instance by displaying a series of selections ranked according to rank order; selections displayed per category, such as without limitation a display of a first set of potential breakfast selections in order of ranking as applicable to breakfast selections, a second set of potential lunch selections in order of ranking as applicable to lunch selections, and/or a set of potential dinner selections in order of ranking as applicable to dinner selections.

Still referring to FIG. 1, displaying may include recommending one or more provider ingredient combinations 120, such as combinations corresponding to one or more meals for which user has not yet made a selection. Recommendations 152 may be generated according to ranking and/or past user selection; for instance, user datastore 148 may contain records of past user selections as well as data and/or metadata such as meals for which selections were performed, days of the week on which user made such selections, times of year at which user made selections, or the like, each of which may be matched to data and/or metadata corresponding to a meal for which recommendations 152 are made. Recommendations 152 may be presented, without limitation, as a proposed meal schedule for a user to follow. Each ranked and/or recommended ingredient combination may be displayed as a link, in conjunction with a checkbox, radio button, or the like, or otherwise in any manner permitting user to enter a selection of one or more displayed elements With continued reference to FIG. 1, computing device 104 may be configured to recommend one or more of plurality of candidate ingredient combinations 144 and/or provider ingredient combinations 120 by identifying one or more goal parameters and selecting utilizing the one or more goal parameters. As used in this disclosure, a "goal parameter" is a datum, other than a nutrient quantity, describing a candidate ingredient combination. A goal parameter may include, without limitation, a time of delivery of a candidate ingredient combination, an amount of time to prepare a candidate ingredient combination, an identity of a dish to be prepared using candidate ingredient combination, a cost of candidate ingredient combination 144 and/or provider ingredient combination 120 such as a cost to be paid to a user, a cost of delivery, a delivery transit time, and/or a rating such as a quantitative rating of a preparer such as a chef, a quantitative rating of the dish, a quantitative rating of the alimentary provider, a quantitative rating of a delivery service, or the like. Qualitative ratings may include customer ratings collected using customer satisfaction surveys, expert ratings by reviewers, or the like.

Still referring to FIG. 1, at least a goal parameter may include at least a default parameter; for instance, as a default, computing device 104 may set as goal parameters a minimal cost, a delivery time below a certain threshold, and maximal qualitative ratings for one or more aspects of delivery. Alternatively or additionally, computing device 104 may receive at least a user parameter and select at least a recommended ingredient combination from the plurality of candidate ingredient combinations 144 to match the at least a user parameter; user parameter may, for instance be added to and/or used to modify at least a default goal parameter. For instance, user may set as a goal parameter a particular dish the user is interested in consuming; user may select the dish, for instance and without limitation by being provided a list of dishes representing beneficial ingredient combinations, e.g. by being composed of ingredients of a beneficial ingredient combination, and selecting one displayed dish. User may set a particular price range, a particular delivery time and/or duration, or the like that interests the user. User may also provide inputs describing relative importance to user of each goal parameter, whether set by system 100 or user entered.

Further referring to FIG. 1, computing device 104 may receive provider parameters from alimentary provider devices 124a-n; parameter parameters may include values corresponding to any or all categories of goal parameters as described above. In an embodiment, provider parameters may be viewed as "bids" from alimentary providers seeking to have services and/or products utilized by user via system 100; bids and/or sets of provider parameters may be compared to any or all goal parameters to select an alimentary provider to provide user with a meal matching a candidate ingredient set. Some provider parameters may not be provided by an alimentary provider itself; for instance, provider parameters may include qualitative reviews from third party sites and/or devices. As a further example, delivery options, times, costs, or the likes may be provided directly by alimentary provider and/or by one or more devices operated by and/or used by one or more third-party delivery services.

With continued reference to FIG. 1, computing device 104 may perform machine-learning algorithms using a loss function analysis to select each recommended ingredient combination from plurality of candidate ingredient combinations 144. In an embodiment, computing device 104 may compare one or more user specific inputs to a mathematical expression representing a plurality of goal parameters. Mathematical expression may include a linear combination of variables, weighted by coefficients representing relative importance of each goal parameter. For instance, a variable such as food quality, importance to user of organic ingredients versus nonorganic ingredients may be multiplied by a first coefficient representing the importance of organic food standards, a second user input such as total cost may be multiplied by a second coefficient representing the importance of cost, a degree of variance from a and/or classified beneficial ingredient set may be represented as another parameter, which may be multiplied by another coefficient representing the importance of that parameter, a degree of variance from a preference for fresh or frozen ingredients may be multiplied by an additional coefficient representing an importance of that parameter, or the like; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, computing device 104 may calculate variables of set of provider parameters and/or variance of such parameters from goal parameters calculate an output of mathematical expression using the variables, and select candidate ingredient combination 144 that produces an output having the lowest size, according to a given definition of "size," of the set of outputs representing each of plurality of candidate ingredient combinations 144; size may, for instance, included absolute value, numerical size, or the like. Selection of different loss functions may result in identification of different candidate ingredient combinations 144 as generating minimal outputs; for instance, where organic ingredients is associated in a first loss function with a large coefficient or weight, a candidate ingredient combination 144 having a small coefficient or weight for organic ingredients may minimize the first loss function, whereas a second loss function wherein organic ingredients has a smaller coefficient but degree of variance from cost goal which has a larger coefficient may produce a minimal output for a different candidate ingredient combination 144 having a larger organic ingredients but more closely hewing to a cost goal.

Alternatively or additionally, and still referring to FIG. 1, each candidate ingredient combination 144 and/or provider ingredient combination may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each parameter. A candidate ingredient combination 144 and/or provider ingredient combination 120 having a mathematical expression minimizing the error function may be selected, as representing an optimal expression of relative importance of parameters to a system or user. In an embodiment, error function and loss function calculations may be combined; for instance, a candidate ingredient combination 144 and/or provider ingredient combination 120 resulting in a minimal aggregate expression of error function and loss function, such as a simple addition, arithmetic mean, or the like of the error function with the loss function, may be selected, corresponding to an option that minimizes total variance from goal parameters while simultaneously minimizing a degree of variance from a set of priorities corresponding to goal parameters. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each parameter to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function, such as without limitation using a regression algorithm. Mathematical expression and/or loss function may be user-specific, using a training set composed of past user selections; mathematical expression and/or loss function may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of candidate ingredient combinations 144. Use of regression to derive loss functions, loss function coefficients, and/or mathematical expressions may be performed, without limitation, as described in U.S. Nonprovisional application Ser. No. 16/502,835.

In an embodiment, and further referring to FIG. 1, computing device 104 may be configured to display ranked list 140 and/or at least a recommended ingredient combination 152 to user. Computing device 104 may receive a user selection of an ingredient combination, for instance by way of user selection of a link, button and/or other display element corresponding to a recommended ingredient combination. Computing device 104 may automatically initiate preparation and/or delivery of selected ingredient combination, for instance and without limitation by transmitting indication of selection to a corresponding alimentary provider device.

Still referring to FIG. 1, computing device 104 is configured to generate a modified ranked list 140 of ingredient combinations as a function of the user selection and the alimentary instruction set 108. Generation of modified ranked list 140 may be performed using any method and/or method steps for generation of ranked list 140 as described above. Modified ranked list 140 may be generated using modified recommended nutrient quantities, where modification of nutrient quantities is performed as a function of selected ingredient combination. For instance, and without limitation, computing device 104 may determine a modified per-meal alimentary instruction set 116 and generate the modified ranked list 140 as a function of the modified per-meal alimentary instruction set 116. As a non-limiting example, any nutrient quantities to be consumed in selected ingredient combination may be subtracted from nutrient quantities of alimentary instruction set 108, after which a new per-meal alimentary instruction set 116 may be determined as above. Alternatively or additionally nutrient quantities corresponding to selected ingredient combination may be divided by a number of meals to be consumed according to schedule and then subtracted from existing per-meal alimentary instruction set 116. Persons skilled in the art, upon reviewing the entirety of this disclosure, will be aware of various ways in which per-meal alimentary instruction set 116 may be modified based on an ingredient combination selection. Computing device 104 may display the modified ranking to user.

Still referring to FIG. 1, in an embodiment, steps described above may be performed iteratively; at each iteration user may select one or more ingredient combinations, upon which computing device 104 may regenerate rankings, display regenerated rankings, generate recommended ingredient combinations, and/or display recommended ingredient combinations. Iteration may be repeated until a period covered by a schedule as described above has been filled with selections. Recommendations 152 may be displayed concurrently with ranked lists 136, for instance and without limitation in separate windows, frames, or the like, permitting user to select recommended ingredient combinations, ingredient combinations from ranked list 140, or the like. Upon presentation with a recommended series of meals, user may accept entire recommended series, accept a subset thereof while rejecting a remainder thereof, accept one or more while selecting other meals from ranked list 140, or rejecting all recommendations 152 and selecting one or more other meals from ranked list 140.

Figure 5:
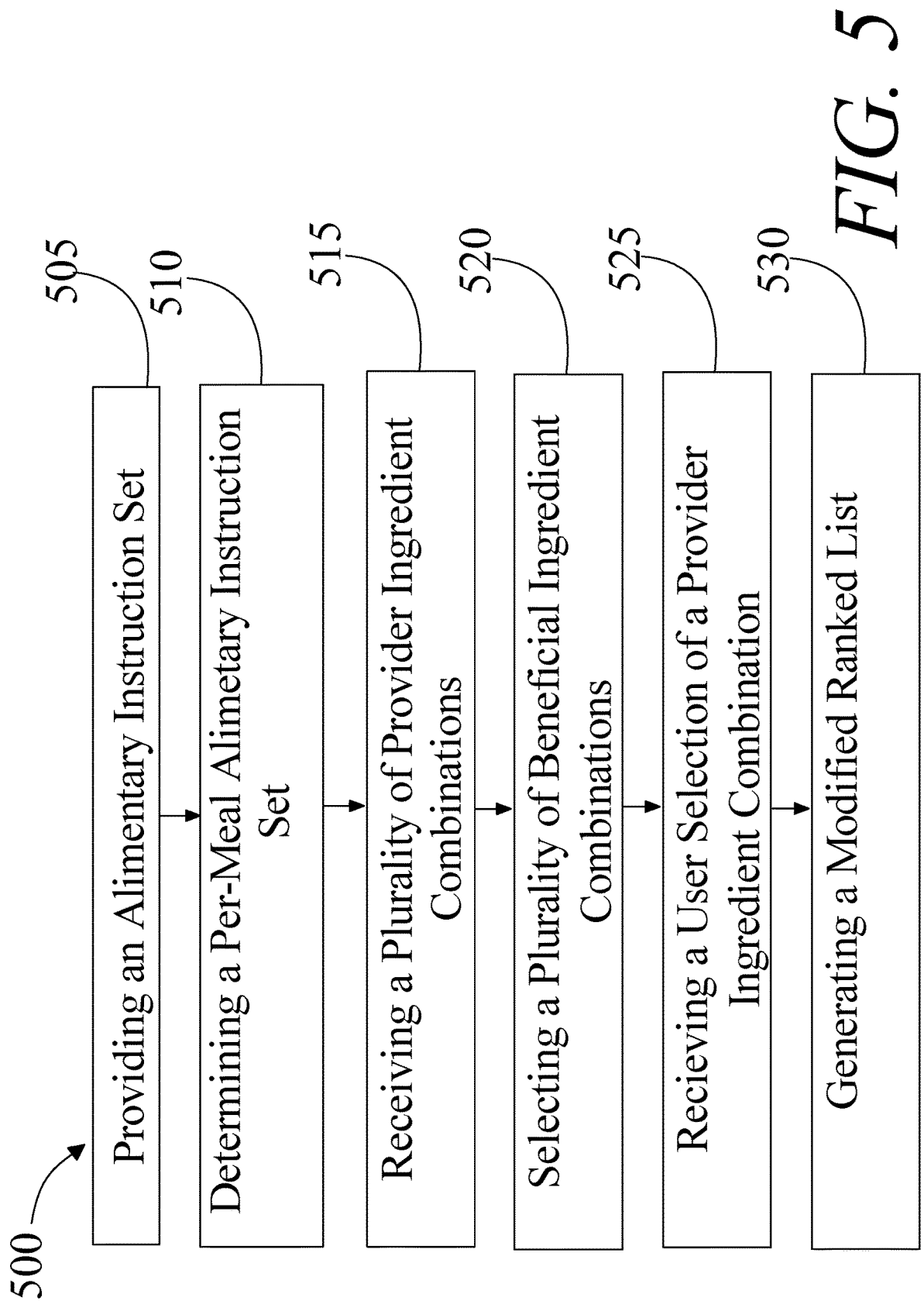
FIG. 5 is a flow diagram of an exemplary embodiment of a method of scheduling alimentary combinations.

Referring now to FIG. 5, an exemplary embodiment of a method 500 of scheduling alimentary combinations is illustrated. At step 505, computing device 104 provides an alimentary instruction set 108 including a plurality of target nutrient quantities 112 corresponding to a plurality of scheduled meals; this may be implemented, without limitation, as described above in reference to FIGS. 1-4. Providing the alimentary instruction set 108 may include receiving training data, recording at least a biological extraction from a user, training a machine-learning process using the training data, and generating the at least an alimentary instruction set 108 as a function of biological extraction and using the machine-learning process, for instance as described above.

At step 510, and still referring to FIG. 5, computing device 104 determines a per-meal alimentary instruction set 116 as a function of the plurality of target nutrient quantities 112; this may be implemented, without limitation, as described above in reference to FIGS. 1-4.

At step 515, and with continued reference to FIG. 5, computing device 104 receives from each alimentary provider device of a plurality of alimentary provider devices 124a-n, a plurality of provider ingredient combinations 120; this may be implemented, without limitation, as described above in reference to FIGS. 1-4.

At step 520, and still referring to FIG. 5, computing device 104 generates a ranked list 140 of ingredient combinations as a function of the plurality of provider ingredient combinations 120; this may be implemented, without limitation, as described above in reference to FIGS. 1-4. Selecting each ingredient combination of the plurality of beneficial ingredient combinations includes determining a nutrient listing corresponding to each ingredient combination of the plurality of provider ingredient combinations 120, creating a distance metric from the nutrient listing to the per-meal alimentary instruction set 116, and selecting at least an ingredient listing that minimizes the distance metric, and ranking the plurality provider ingredient combinations 120 to minimize the distance metric. Generating the ranked list 140 of ingredient combinations may include identifying a plurality of candidate ingredient combinations 144 as a function of the plurality ingredients and generating the ranked list 140 as a function of the plurality of candidate ingredient combinations 144. Identifying the plurality of candidate ingredient combinations 144 may include comparing, for each ingredient combination of the plurality of provider ingredient combinations 120, a distance metric corresponding to the ingredient combinations to a preconfigured threshold, and eliminating each ingredient combination that fails the threshold comparison Identifying the plurality of candidate ingredient combinations 144 may include receiving at least a user parameter and identifying the plurality of candidate ingredient combinations 144 to match the at least a user parameter. Creating distance metric may include generating requirement ingredients corresponding to target nutrition quantities and creating the distance metric from provider ingredient combinations 120 to requirement ingredients. Creating distance metric may include creating a classifier distance metric.

At step 525, and further referring to FIG. 5, computing device 104 receives a user selection of a provider ingredient combination corresponding to a meal of the plurality of scheduled meals; this may be implemented, without limitation, as described above in reference to FIGS. 1-4. Receiving user selection may include displaying the ranked list 140 on a user client device and receiving a user selection of the displayed ranked list 140.

At step 530, and still referring to FIG. 5, computing device 104 generates a modified ranked list 140 of ingredient combinations as a function of user selection and alimentary instruction set 108; this may be implemented, without limitation, as described above in reference to FIGS. 1-4. Generating modified ranked list 140 may include determining a modified per-meal alimentary instruction set 116 and generating the modified ranked list 140 as a function of the modified per-meal alimentary instruction set 116.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
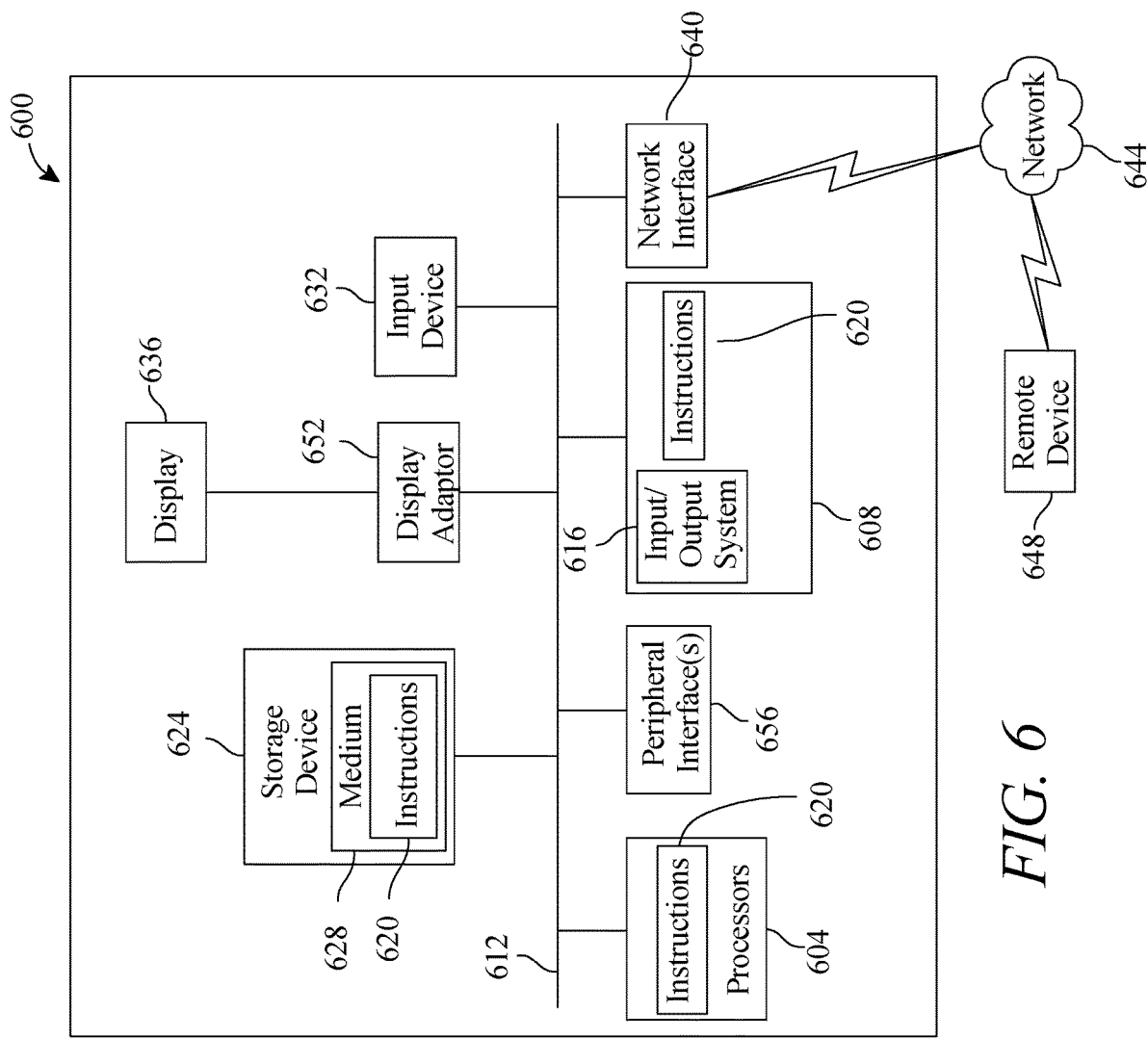
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for scheduling alimentary combinations, the system comprising:
   a sensor, wherein the sensor is configured to:
     detect physiological data of a user as a signal; and
     transmit at least a biological extraction input as a function of the signal to a user device, wherein the biological extraction input comprises a hematological parameter; and
   a computing device, wherein the computing device is configured to:
     provide an alimentary instruction set including a plurality of target nutrient quantities corresponding to a plurality of scheduled meals, wherein providing the alimentary instruction set further comprises:
creating a training dataset comprising a plurality of biological extractions each correlated to a respective target nutrient quantity;
recording the at least a biological extraction input from the user device;
training an artificial neural network using the training dataset, wherein the artificial neural network is configured to receive the at least a biological extraction input as an input and output at least a target nutrient quantity;
inputting the biological extraction input to the artificial neural network;
generating the at least a target nutrient quantity as a function of the biological extraction input and the artificial neural network; and
generating the alimentary instruction set as a function of the at least a target nutrient quantity;
determine a per-meal alimentary instruction set as a function of the plurality of target nutrient quantities;
receive, from each alimentary provider device of a plurality of alimentary provider devices, a plurality of provider ingredient combinations;
generate a ranked list of provider ingredient combinations as a function of the plurality of provider ingredient combinations, wherein generating further comprises:
determining a nutrient listing corresponding to each provider ingredient combination of the plurality of provider ingredient combinations;
creating a distance metric from each nutrient listing to the per-meal alimentary instruction set, wherein creating the distance metric comprises creating a distance metric classifier using a machine-learning model trained iteratively by using a plurality of nutrient quantity training data, wherein the nutrient quantity training data comprises modified sets of nutrient quantities associated with provider ingredient combinations recorded as having been used in meals in a past, and wherein creating the distance metric further comprises:
generating vectors representing a combination of nutrient quantities associated with each ingredient combination, and target nutrient quantities;
determining degrees of similarity between the vectors; and
calculating the distance metric as a function of the degrees of similarity;
selecting at least a nutrient listing that minimizes the distance metric;
generating the ranked list from the plurality of provider ingredient combinations; and
ranking the plurality of provider ingredient combinations within the ranked list to minimize the distance metric;
receive, from the user device, a user selection of a provider ingredient combination corresponding to a meal of the plurality of scheduled meals and at least a goal parameter;
filter the provider ingredient combination, wherein the computing device compares at least one user input to a mathematical expression representing the at least a goal parameter comprising a liner combination of variables weighted by coefficients representing an importance of the at least a goal parameter;
generate a modified ranked list of ingredient combinations as a function of the user selection, the alimentary instruction set and the at least a goal parameter; and
display on the user device a recommended series comprising the modified ranked list of ingredient combinations, wherein the input device is configured to permit the user to:
select the recommended series;
select at least an ingredient combination from the recommended series; and
reject the recommended series.

2. The system of claim 1, wherein the computing device is further configured to generate the ranked list of provider ingredient combinations by:
identifying a plurality of candidate ingredient combinations as a function of the plurality of provider ingredient combinations; and
generating the ranked list as a function of the plurality of candidate ingredient combinations.

3. The system of claim 2, wherein identifying the plurality of candidate ingredient combinations further comprises:
comparing, for each ingredient combination of the plurality of provider ingredient combinations, a distance metric corresponding to the ingredient combinations to a preconfigured threshold; and
eliminating each ingredient combination that fails the threshold comparison.

4. The system of claim 2 wherein identifying the plurality of candidate ingredient combinations further comprises:
receiving at least a user parameter; and
identifying the plurality of candidate ingredient combinations to match the at least a user parameter.

5. The system of claim 1, wherein creating the distance metric further comprises:
generating requirement ingredients corresponding to target nutrition quantities; and
creating the distance metric from each provider ingredient combination to the requirement ingredients.

6. The system of claim 1, wherein creating the distance metric further comprises creating a classifier distance metric.

7. The system of claim 1, wherein the computing device is further configured to receive the user selection by:
displaying the ranked list on the user device; and
receiving the user selection of an element of the displayed ranked list.

8. The system of claim 1, wherein the computing device is configured to generate the modified ranked list by:
determining a modified per-meal alimentary instruction set; and
generate the modified ranked list as a function of the modified per-meal alimentary instruction set.

9. The system of claim 1, wherein the computing device is configured to display the modified ranked list to the user device.

10. A method of scheduling alimentary combinations, the method comprising:
detecting, by a sensor, physiological data of a user as a signal; and
transmitting, by the sensor, at least a biological extraction input as a function of the signal to a user device, wherein the biological extraction input comprises a hematological parameter;
providing, by a computing device, an alimentary instruction set including a plurality of target nutrient quantities corresponding to a plurality of scheduled meals, wherein providing the alimentary instruction set further comprises:
  creating a training dataset comprising a plurality of biological extractions each correlated to a respective target nutrient quantity;
  recording the at least a biological extraction input from the user device;
  training an artificial neural network using the training dataset, wherein the artificial neural network is configured to receive the at least a biological extraction input as an input and output at least a target nutrient quantity;
  inputting the biological extraction input to the trained machine-learning model;
  generating the at least a target nutrient quantity as a function of the biological extraction input and the artificial neural network; and
  generating the alimentary instruction output set as a function of the at least a target nutrient quantity;
determining, by the computing device, a per-meal alimentary instruction set as a function of the plurality of target nutrient quantities;
receiving, by the computing device, from each alimentary provider device of a plurality of alimentary provider devices, a plurality of provider ingredient combinations;
generating, by the computing device, a ranked list of provider ingredient combinations as a function of the plurality of provider ingredient combinations, wherein generating further comprises:
  determining a nutrient listing corresponding to each provider ingredient combination of the plurality of provider ingredient combinations;
  creating a distance metric from each nutrient listing to the per-meal alimentary instruction set, wherein creating the distance metric comprises creating a distance metric classifier using a machine-learning model trained iteratively by using a plurality of nutrient quantity training data, wherein the nutrient quantity training data comprises modified sets of nutrient quantities associated with provider ingredient combinations recorded as having been used in meals in the past, and wherein creating the distance metric further comprises:
    generating vectors representing a combination of nutrient quantities associated with each ingredient combination, and target nutrient quantities;
    determining degrees of similarity between the vectors; and
    calculating the distance metric as a function of the degrees of similarity;
  selecting at least a nutrient listing that minimizes the distance metric;
  generating the ranked list from the plurality of provider ingredient combinations; and
  ranking the plurality of provider ingredient combinations within the ranked list to minimize the distance metric;
receiving, by the computing device from the user device, a user selection of a provider ingredient combination corresponding to a meal of the plurality of scheduled meals and at least a goal parameter;
filtering, by the computing device, the provider ingredient combination, wherein the computing device compares at least one user input to a mathematical expression representing the at least a goal parameter comprising a liner combination of variables weighted by coefficients representing an importance of the at least a goal parameter;
generating, by the computing device, a modified ranked list of ingredient combinations as a function of the user selection, the alimentary instruction set and the at least a goal parameter; and
displaying, on the user device, a recommended series comprising the modified ranked list of ingredient combinations, wherein the input device is configured to permit the user to:
  select the recommended series;
  select at least an ingredient combination from the recommended series; and
  reject the recommended series.

11. The method of claim 10, wherein generating the ranked list of provider ingredient combinations further comprises:
  identifying a plurality of candidate ingredient combinations as a function of the plurality of provider ingredient combinations; and
  generating the ranked list as a function of the plurality of candidate ingredient combinations.

12. The method of claim 11, wherein identifying the plurality of candidate ingredient combinations further comprises:
  comparing, for each ingredient combination of the plurality of provider ingredient combinations, a distance metric corresponding to the ingredient combinations to a preconfigured threshold; and
  eliminating each ingredient combination that fails the threshold comparison.

13. The method of claim 11 wherein identifying the plurality of candidate ingredient combinations further comprises:
  receiving at least a user parameter; and
  identifying the plurality of candidate ingredient combinations to match the at least a user parameter.

14. The method of claim 10, wherein creating the distance metric further comprises:
  generating requirement ingredients corresponding to target nutrition quantities; and
  creating the distance metric from each provider ingredient combination to the requirement ingredients.

15. The method of claim 10, wherein creating the distance metric further comprises creating a classifier distance metric.

16. The method of claim 10, wherein receiving the user selection further comprises:
  displaying the ranked list on the user device; and
  receiving the user selection of an element of the displayed ranked list.

17. The method of claim 10, wherein generating the modified ranked list further comprises:
  determining a modified per-meal alimentary instruction set; and
  generate the modified ranked list as a function of the modified per-meal alimentary instruction set.

18. The method of claim 10, wherein the computing device is configured to display the modified ranked list to the user device.

19. The system of claim 1, wherein the sensor is part of a wearable device worn by the user, and wherein the hematological parameter comprises at least one of a blood oxygen level, pulse rate, heart rate, pulse rhythm, blood sugar and blood pressure.

20. The method of claim 10, wherein the sensor is part of a wearable device worn by the user, and wherein the hematological parameter comprises at least one of a blood oxygen level, pulse rate, heart rate, pulse rhythm, blood sugar and blood pressure.

\* \* \* \* \*